United States Patent
Wankhede et al.

(10) Patent No.: US 9,556,174 B2
(45) Date of Patent: Jan. 31, 2017

(54) (2S, 5R)-SULFURIC ACID MONO-{[(4-AMINOPIPERIDIN-4-YL) CARBONYL]-7-OXO-1,6-DIAZA-BICYCLO [3.2.1]-OCT-6-YL} ESTER

(71) Applicant: WOCKHARDT LIMITED, Aurangabad (IN)

(72) Inventors: Karuna Suresh Wankhede, Aurangabad (IN); Mahesh Manikrao Surwase, Latur (IN); Satish Bhawsar, Aurangabad (IN); Prasad Keshav Deshpande, Aurangabad (IN); Ravindra Dattatraya Yeole, Aurangabad (IN); Mahesh Vithalbhai Patel, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 14/769,805

(22) PCT Filed: Oct. 12, 2013

(86) PCT No.: PCT/IB2013/059329
§ 371 (c)(1),
(2) Date: Aug. 22, 2015

(87) PCT Pub. No.: WO2015/033191
PCT Pub. Date: Mar. 12, 2015

(65) Prior Publication Data
US 2016/0002233 A1 Jan. 7, 2016

(30) Foreign Application Priority Data

Mar. 8, 2013 (IN) .......................... 716/MUM/2013

(51) Int. Cl.
*C07D 471/08* (2006.01)
(52) U.S. Cl.
CPC .................. *C07D 471/08* (2013.01)
(58) Field of Classification Search
CPC .................................................. C07D 471/08
USPC ....................................................... 546/121
See application file for complete search history.

(56) References Cited

FOREIGN PATENT DOCUMENTS

| EP | 2657234 | * | 10/2013 |
| WO | 2009091856 | * | 7/2009 |
| WO | WO2009091856 A1 | | 7/2009 |
| WO | 2012086241 | * | 6/2012 |
| WO | WO2012086241 A1 | | 6/2012 |

OTHER PUBLICATIONS

Mangion et al., A concise synthesis of a-lactamase inhibitor.Org Lett. Oct. 21, 2011;13(20):5480-3. doi: 10.1021/o1202195n. Epub Sep. 15, 2011.
Valeur et al., Amide bond formation: beyond the myth of coupling reagents. Chem Soc Rev. Feb. 2009;38(2):606-31. doi: 10.1039/b701677h. Epub Dec. 4, 2008.

* cited by examiner

*Primary Examiner* — Patricia L Morris
(74) *Attorney, Agent, or Firm* — Bio Intelectual Property Services LLC (Bio IPS); O. (Sam) Zaghmout

(57) ABSTRACT

A process for preparation of (2S, 5R)-Sulfuric acid mono-{[(4-aminopiperidin-4-yl) carbonyl]-7-oxo-1,6-diaza-bicyclo[3.2.1]-oct-6-yl} ester is disclosed which comprises reacting a compound of Formula (II) with a compound of Formula (III) to obtain a compound of Formula (IV).

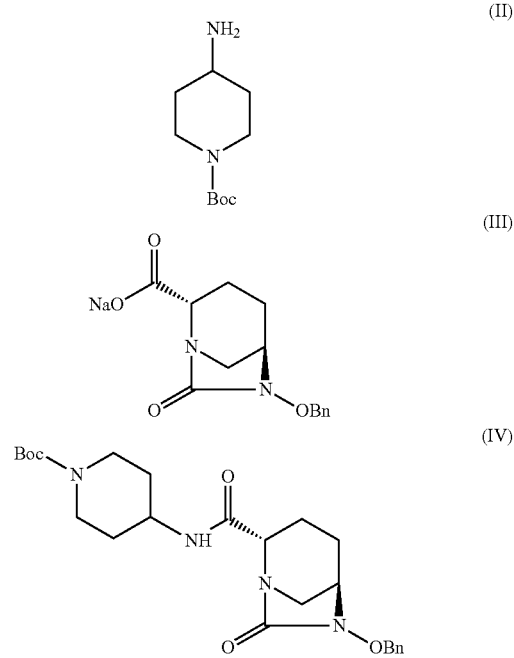

6 Claims, No Drawings

(2S, 5R)-SULFURIC ACID MONO-{[(4-AMINOPIPERIDIN-4-YL) CARBONYL]-7-OXO-1,6-DIAZA-BICYCLO [3.2.1]-OCT-6-YL} ESTER

RELATED PATENT APPLICATIONS

This application claims benefit of Indian Patent Application No. 716/MUM/2013 filed on Mar. 8, 2013, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to a process for preparation of (2S, 5R)-Sulfuric acid mono-{[(4-aminopiperidin-4-yl) carbonyl]-7-oxo-1,6-diaza-bicyclo[3.2.1]-oct-6-yl} ester.

BACKGROUND OF THE INVENTION

A compound of Formula (I), chemically known as (2S, 5R)-Sulfuric acid mono-{[(4-aminopiperidin-4-yl) carbonyl]-7-oxo-1,6-diaza-bicyclo[3.2.1]-oct-6-yl} ester has antibacterial properties. The compound of Formula (I) is also known as MK-7655 and is disclosed in PCT International Patent Application No PCT/US2009/031047.

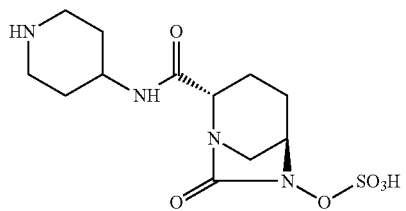

Formula (I)

SUMMARY OF THE INVENTION

In one general aspect, there is provided a process for preparation of a compound of Formula (I), comprising:

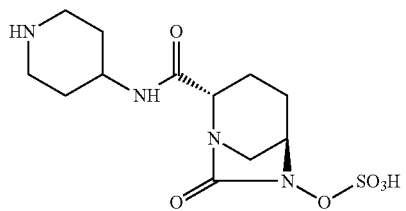

Formula (I)

(a) reacting a compound of Formula (II) with a compound of Formula (III) to obtain a compound of Formula (IV);

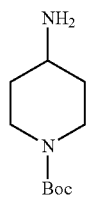

Formula (II)

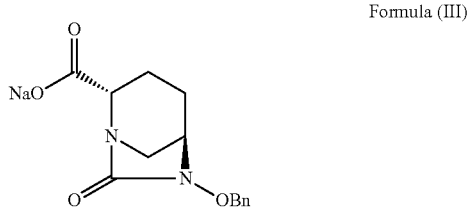

Formula (III)

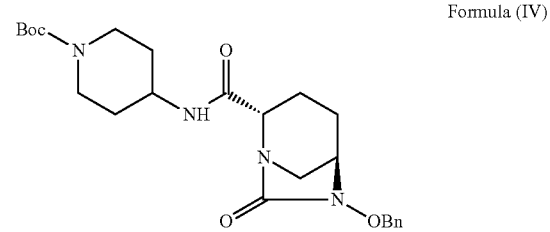

Formula (IV)

(b) hydrogenolysis of a compound of Formula (IV) to obtain a compound of Formula (V);

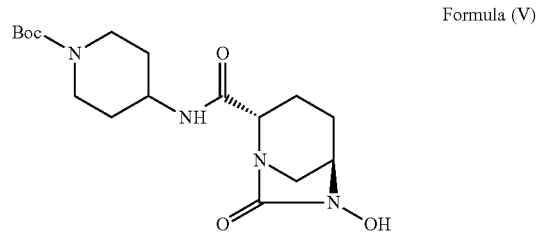

Formula (V)

(c) sulfonating a compound of Formula (V) to obtain a compound of Formula (VI); and

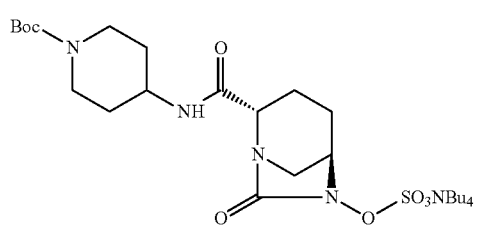

Formula (VI)

(d) converting a compound of Formula (VI) into a compound of Formula (I).

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

The term "HOBt" as used herein refers to 1-hydroxybenzotriazole.

The term "EDC" as used herein refers to 1-ethyl-3-(3-dimethylaminopropyl) carbodiimide.

In one general aspect, there is provided a process for preparation of a compound of Formula (I), comprising:

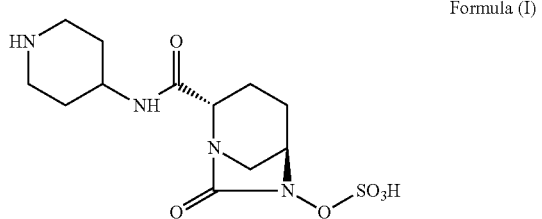 [SMILES: O=C(NC1CCNCC1)[C@@H]1CC[C@@H]2CN1C(=O)N2OS(=O)(=O)O]

Formula (I)

(a) reacting a compound of Formula (II) with a compound of Formula (III) to obtain a compound of Formula (IV);

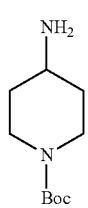

Formula (II)

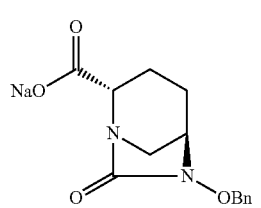

Formula (III)

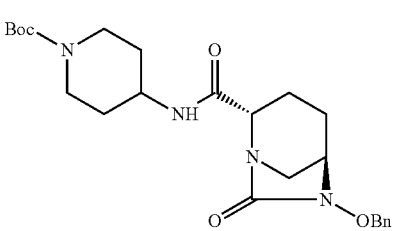

Formula (IV)

(b) hydrogenolysis of a compound of Formula (IV) to obtain a compound of Formula (V);

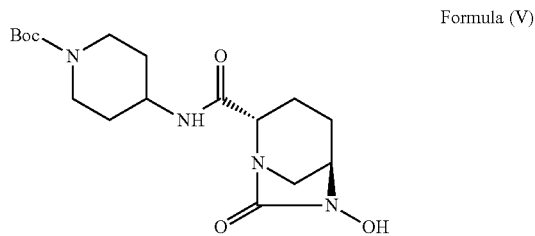 [SMILES: CC(C)(C)OC(=O)N1CCC(NC(=O)[C@@H]2CC[C@@H]3CN2C(=O)N3O)CC1]

Formula (V)

(c) sulfonating a compound of Formula (V) to obtain a compound of Formula (VI); and

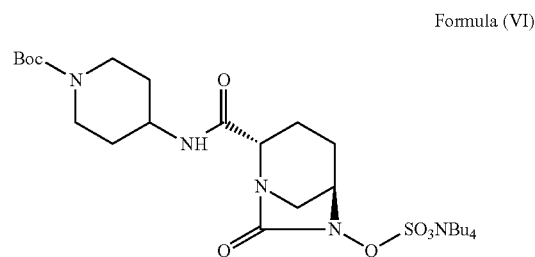

Formula (VI)

(d) converting a compound of Formula (VI) into a compound of Formula (I).

The compound of Formula (IV) is obtained by reacting a compound of Formula (II) with a compound of Formula (III). In some embodiments, the compound of Formula (IV) is obtained by reacting a compound of Formula (II) with a compound of Formula (III) in presence of a suitable coupling reagent. In some other embodiments, the compound of Formula (IV) is obtained by reacting a compound of Formula (II) with a compound of Formula (III) in presence of 1-hydroxybenzotriazole and 1-ethyl-3-(3-dimethylaminopropyl)carbodiimide hydrochloride. This reaction may be carried out in presence of a suitable solvent. In some embodiments, this reaction is carried out in water as a reaction solvent.

The compound of Formula (V) is obtained by hydrogenolysis of a compound of Formula (IV). The hydrogenolysis reaction can be carried out using a suitable hydrogenolysis agent. In some embodiments, hydrogenolysis of a compound of Formula (IV) to obtain a compound of Formula (V) is carried out in presence of a transition metal catalyst and hydrogen source. In some other embodiments, the transition metal catalyst is palladium on carbon and hydrogen source is hydrogen gas. In some other embodiments, the hydrogenolysis reaction is carried out in presence of a suitable solvent such as, for example, methanol. In some embodiments, the hydrogenolysis of a compound of Formula (IV) to obtain a compound of Formula (V) is carried out using 10% palladium on carbon catalyst, in presence of hydrogen gas in methanol as a solvent.

The compound of Formula (VI) is obtained by sulfonating a compound of Formula (V). The sulfonation reaction can be carried out in presence of a suitable solvent. In some embodiments, the sulfonation of a compound of Formula (V) to obtain a compound of Formula (VI) is carried out by reacting a compound of Formula (V) with sulfur trioxide-pyridine complex, followed by treatment with tetrabutyl ammonium hydrogen sulphate.

The compound of Formula (VI) is converted to a compound of Formula (I) in presence of a suitable reagent. In some embodiments, the compound of Formula (VI) is converted to a compound of Formula (I) by reacting a compound of Formula (VI) with trifluoroacetic acid.

In some embodiments, the compound of Formula (I) is prepared using a process described in Scheme 1.

sitions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

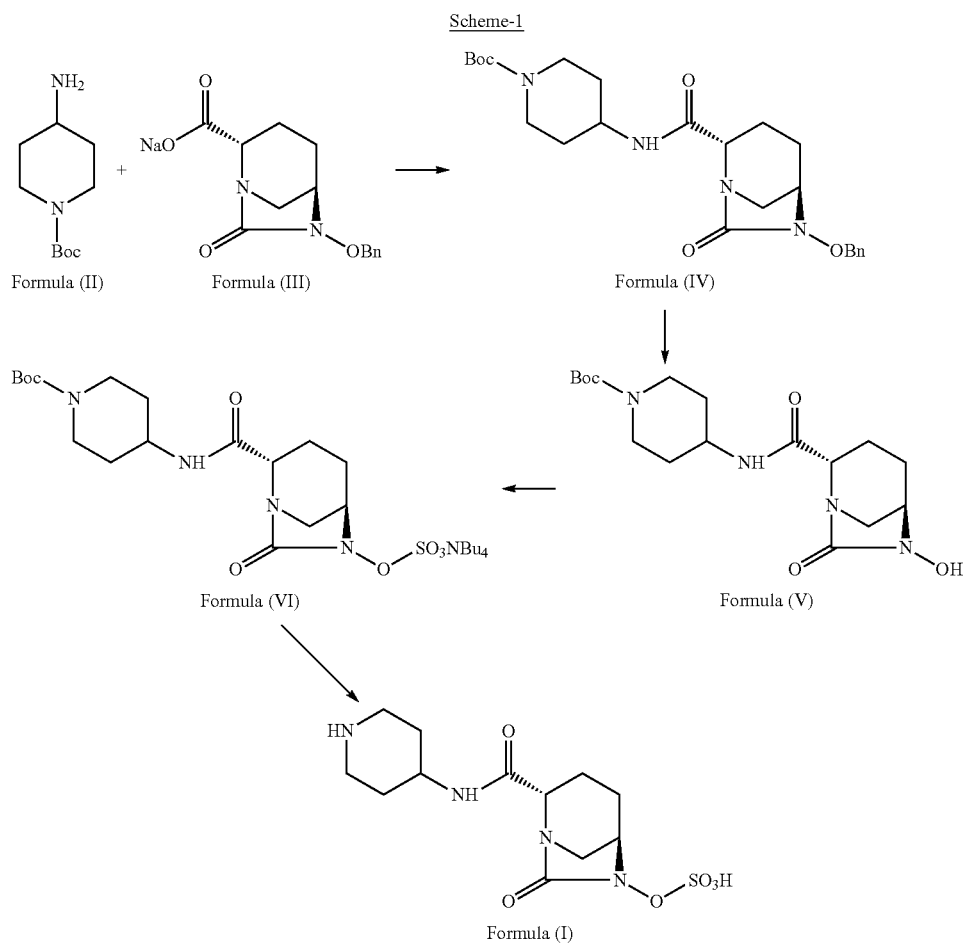

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compo- Example-1

Preparation of (2S, 5R)-Sulfuric acid mono-{2-[N'-(4-aminopiperidinyl)-carbonyl]-7-oxo-1,6-diaza-bicyclo[3.2.1]oct-6-yl} ester (I)

Step-1: Preparation of (2S, 5R)-tert-butyl {(6-benzyloxy-7-oxo-1,6-diaza-bicyclo[3.2.1]oct-2-yl-carbonyl) amino} piperidine-1-carboxylate (IV)

To a 250 ml round bottom flask equipped with magnetic stirrer was charged a solution of (2S, 5R)-sodium 6-benzyloxy-7-oxo-1,6-diaza-bicyclo [3.2.1] octane-2-carboxylate (11.1 gm, 0.037 mol, prepared using a method disclosed in Indian Patent Application No 699/MUM/2013) in water (180 ml) followed by 1-tert-butoxycarbonyl-4-amino-piperidine (7.8 gm, 0.039 mol), EDC hydrochloride (11 gm, 0.055 mol) and 1-hydroxybenzotriazole (4.8 gm, 0.037 mol)

at 30° C. successively under stirring. The reaction mixture was stirred for 24 hours at 30° C. to provide a suspension. The suspension was filtered under suction and washed with 45° C. warm water (40 ml) to provide (2S, 5R)-tert-butyl {(6-benzyloxy-7-oxo-1,6-diaza-bicyclo[3.2.1]oct-2-yl-carbonyl) amino} piperidine-1-carboxylate in 12.7 gm quantity in 74% yield after drying under vacuum.

Analysis

NMR: (CDCl3,)=7.36-7.44 (m, 5H), 6.56 (d, 1H), 5.06 (d, 1H), 4.91 (d, 1H), 4.03 (br s, 1H), 3.88-3.97 (m, 2H), 3.29 (s, 1H), 3.00 (d, 1H), 2.86 (t, 2H), 2.64 (d, 1H), 2.37 (dd, 1H), 1.85-2.01 (m, 4H), 1.54-1.62 (m, 2H), 1.45 (s, 9H), 1.25-1.36 (m, 2H).

MS (ES+) C24H34N4O5=459.5 (M+1).

Step-2: Preparation of (2S, 5R)-tert-butyl {(6-hydroxy-7-oxo-1,6-diaza-bicyclo[3.2.1]oct-2-yl-carbonyl) amino} piperidine-1-carboxylate (V)

To a 100 ml single neck round bottom flask equipped with magnetic stirrer was charged a solution of (2S, 5R)-tert-butyl {(6-benzyloxy-7-oxo-1,6-diaza-bicyclo[3.2.1]oct-2-yl-carbonyl) amino} piperidine-1-carboxylate (9 g, 19.5 mmol) in methanol (90 ml) followed by 10% palladium on carbon (2.7 g) at 35° C. The reaction mixture was stirred under 1 atm hydrogen pressure at 35° C. for 2 hours. The catalyst was removed by filtering the reaction mixture under suction over a celite bed. The celite bed was washed with dichloromethane (50 ml). The combined filtrate was evaporated under vacuum below 35° C. to provide (2S, 5R)-tert-butyl {(6-hydroxy-7-oxo-1,6-diaza-bicyclo[3.2.1]oct-2-yl-carbonyl) amino} piperidine-1-carboxylate in 8.45 g quantity; it was used as such for the next reaction.

Analysis

NMR: (CDCl3,)=6.60 (d, 1H), 3.88-4.10 (m, 4H), 3.78 (s, 1H), 3.20 (d, 1H), 3.90 (t, 2H), 2.80 (d, 1H), 2.46 (dd, 1H), 2.1-2.2 (m, 1H), 2.85-2.20 (m, 4H), 1.70-1.80 (m, 1H), 2.47 (s, 9H), 1.30-1.41 (m, 3H).

MS (ES+) C17H28N4O5=369.4 (M+1).

Step-3: Preparation of Tetrabutyl ammonium salt of (2S, 5R)-tert-butyl {(6-sulfooxy-7-oxo-1,6-diaza-bicyclo[3.2.1]oct-2-yl-carbonyl) amino} piperidine-1-carboxylate (VI)

To a 100 ml single neck round bottom flask equipped with magnetic stirrer was charged a solution of (2S, 5R)-tert-butyl {(6-hydroxy-7-oxo-1,6-diaza-bicyclo[3.2.1]oct-2-yl-carbonyl) amino} piperidine-1-carboxylate (6.40 g, 7.6 mmol) in dichloromethane (90 ml), triethyl amine (9.3 ml), followed by pyridine—sulfur trioxide complex (5.4 g, 34.2 mmol) at 35° C. under stirring. The reaction mixture was stirred for additional 4 hours at 35° C. The solvent was evaporated under vacuum below 40° C. to provide a residue. The residue was stirred with 0.5N aqueous potassium dihydrogen phosphate solution (90 ml) for 1 hour. The resulting solution was extracted with dichloromethane (2×100 ml) to remove impurities. To the aqueous layer was added tetrabutyl ammonium hydrogen sulfate (6.9 g, 20.52 mmol) and the reaction mixture was stirred for 14 hours at 35° C. It was extracted with dichloromethane (3×30 ml). Combined organic layer was dried over sodium sulfate and evaporated under vacuum to provide tetrabutyl ammonium salt of (2S, 5R)-tert-butyl {(6-sulfooxy-7-oxo-1,6-diaza-bicyclo[3.2.1]oct-2-yl-carbonyl) amino} piperidine-1-carboxylate in 8.0 g quantity in 62% yield.

Analysis

NMR: (CDCl3,)=6.64 (d, 1H), 4.36 (br s, 1H), 4.05 (br s, 2H), 3.90-4.00 (m, 1H), 3.87 (d, 1H), 2.28-3.34 (m, 10H), 3.80-3.95 (m, 2H), 3.74 (d, 1H), 2.42 (dd, 1H), 2.15-2.24 (m, 1H), 1.82-1.97 (m, 4H), 1.61-1.74 (m, 14H), 1.41-1.52 (m, 10H), 1.02 (t, 12H).

MS (ES−) C17H27N4O8S. N(C4H9)4=447.4 (M−1) as a free sulfonic acid.

Step-4: Synthesis of (2S, 5R)-Sulfuric acid mono-{[(4-aminopiperidin-4-yl) carbonyl]-7-oxo-1,6-diaza-bicyclo[3.2.1]-oct-6-yl} ester (I)

To a 100 ml round bottom flask equipped with magnetic stirrer was charged a solution of tetrabutyl ammonium salt of (2S, 5R)-tert-butyl {(6-sulfooxy-7-oxo-1,6-diaza-bicyclo[3.2.1]oct-2-yl-carbonyl) amino} piperidine-1-carboxylate (6.0 g) in dichloromethane (15 ml). The solution was cooled to −10° C. under stirring and to it was added trifluoroacetic acid (15 ml) drop wise. The reaction mixture was stirred at −10° C. for 1 hour. Solvents were evaporated under vacuum below 30° C. to its ⅓ volume to provide a thick residue. The thick residue was stirred twice with diethyl ether (60 ml each time) to provide a precipitation. The solid obtained was filtered at suction and suspended in acetone (90 ml). To the suspension was added 10% solution of sodium-2-ethyl-hexanoate in acetone to adjust pH between 4.5 to 5.5. The suspension was stirred for 10 minutes and filtered under suction. The wet cake was washed with acetone and dried under vacuum below 40° C. to provide 3 gm crude compound. The crude compound was stirred with aqueous isopropanol (3 ml water: 21 ml iospropanol) for overnight to purify further. The resulting suspension was filtered under suction and washed with aqueous isopropanol (1 ml water: 7 ml IPA mixture). Finally the cake was dried under vacuum below 40° C. to provide the title compound as a off-white solid in 1.8 g quantity in 65% yield.

Analysis

H1NMR (DMSO-d6, D2O exchange)=8.19 (d, exchanges with D2O), 3.99 (s, 1H), 3.82-3.92 (m, 1H), 3.72 (d, 1H), 2.24 (br d, 3H), 2.90-3.04 (m, 5H), 1.96-2.06 (m, 1H), 1.80-1.94 (m, 3H), 1.58-1.72 (m, 4H).

MS (ES+) C12H20N4O6S=349.2 (M+1) as a free sulfonic acid;

Purity by HPLC: 99.2%

Specific rotation: $[\alpha]^{25}_D$ −45.25°, (c 0.3%, water)

We claim:

1. A process for preparation of a compound of Formula (I), comprising:

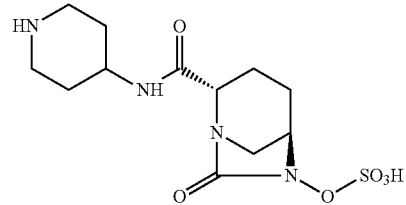

Formula (I)

reacting a compound of Formula (II) with a compound of Formula (III) in presence of a solvent to obtain a compound of Formula (IV) wherein Boc is a tert-butyloxycarbonyl and wherein OBn is a benzyloxy;

Formula (II)

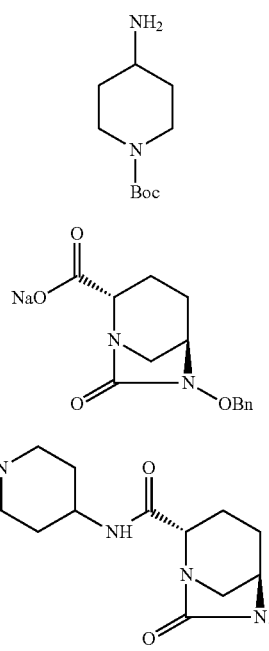

Formula (III)

Formula (IV)

(b) hydrogenolysis of a compound of Formula (IV) to obtain a compound of Formula (V);

Formula (V)

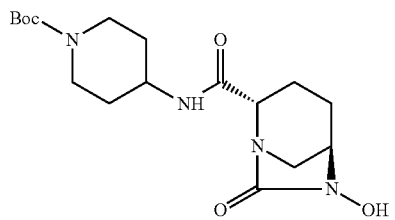

(c) sulfonating a compound of Formula (V) to obtain a compound of Formula (VI); and Formula (VI)

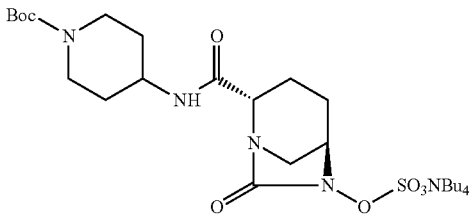

(d) reacting a compound of Formula (VI) with trifluoracetic acid to obtain a compound of Formula (I).

2. The process according to claim 1, wherein a compound of Formula (IV) is obtained by reaction a compound of Formula (II) with a compound of Formula (III) in presence of 1-ethyl-3-(3-dimethylaminopropyl)carbodiimide and 1-hydroxybenzotriazole.

3. A process according to claim 2, wherein the reaction is carried out in presence of water as a solvent.

4. The process according to claim 1, wherein the hydrogenolysis of a compound of Formula (IV) to obtain a compound of Formula (V) is carried out in presence of a transition metal catalyst and hydrogen source.

5. The process according to claim 4, wherein the transition metal catalyst is palladium on carbon and hydrogen source is hydrogen gas.

6. The process according to claim 1, wherein the sulfonation of a compound of Formula (V) to obtain a compound of Formula (VI) is carried out by reacting a compound of Formula (V) with sulfur trioxide-pyridine complex, followed by treatment with aqueous tetrabutyl ammonium hydrogen sulphate.

* * * * *